United States Patent [19]

Klundt

[11] Patent Number: 5,477,794
[45] Date of Patent: Dec. 26, 1995

[54] SUTURING APPARATUS

[75] Inventor: Kurt Klundt, Hirschborn, Germany

[73] Assignee: J. Strobel & Sohne GmbH & Co., Munich, Germany

[21] Appl. No.: 220,507

[22] Filed: Mar. 31, 1994

[30] Foreign Application Priority Data

Mar. 31, 1993 [DE] Germany ............... 43 10 582.3

[51] Int. Cl.$^6$ ................................. D05B 97/08
[52] U.S. Cl. ............................. 112/169; 606/144
[58] Field of Search ................... 606/144, 139, 606/145, 147; 112/169, 162, 176, 177, 322, 197, 199

[56] References Cited

U.S. PATENT DOCUMENTS

| | | | |
|---|---|---|---|
| 4,406,237 | 9/1983 | Eguchi et al. ...................... | 112/169 |
| 4,440,171 | 4/1984 | Nomoto et al. ..................... | 112/169 X |
| 4,747,358 | 5/1988 | Moll et al. . | |
| 4,841,888 | 6/1989 | Mills et al. ........................ | 112/169 |

Primary Examiner—Peter Nerbun
Attorney, Agent, or Firm—Bacon & Thomas

[57] ABSTRACT

A suturing apparatus for connecting tissue edges using a single-thread overcast stitch arrangement incorporates an arc needle and a forked rocking gripper provided at an end of a gripper rod that passes through an aperture in the front wall of the apparatus housing. The needle and the gripper are driven in a rocking motion and cooperate to form the stitches with the arc needle transversely piercing the tissue edges and the gripper being displaceable along an arcuate path over the tissue edges. The gripper rod passes through the front wall of the apparatus housing at which it is connected through a universal joint. The gripper rod is displaceable inside the apparatus housing along a path that is symmetrical to the arcuate path of the rocking gripper.

17 Claims, 4 Drawing Sheets

5,477,794

SUTURING APPARATUS

BACKGROUND OF THE INVENTION

1. Field of the Invention

The present invention is directed to a suturing apparatus adapted to join edges of tissue using a single-thread overcast stitching mechanism.

2. Discussion of the Prior Art

A suturing apparatus is known as disclosed in U.S. Pat. No. 4,747,358 wherein a gripper rod is irrotatably, but axially displaceably, fastened in a swivel plate extending transversely to the gripper rod and to a needle shaft that is parallel to the gripper rod. The swivel plate is guided along a housing wall of the apparatus such that the gripper rod translates in an arcuate path when the swivel plate is pivoted by a radial arm of the needle shaft. The gripper rod can be axially displaced within the swivel plate by a helical gear supported for rotation about an axis perpendicular to the needle shaft and the gripper rod. The helical gear meshes with another helical gear affixed to the needle shaft and, by means of an eccentric cam pin, engages a radial fork at an end of the gripper rod located remote from a rocking gripper carried by the other end of gripper rod.

SUMMARY OF THE INVENTION

The object of the present invention is to provide a suturing apparatus wherein the drive of the rocking gripper is improved. This object is achieved by providing a suturing apparatus for use in joining tissue edges using single-thread overcast stitches wherein the apparatus includes a housing having a front wall through which a first end of a gripper rod projects. A second end of the gripper rod is positioned within the housing and the gripper rod is supported intermediate the first and second ends by a joint that permits pivotal, rotatable and axial shiftable movement of the gripper rod relative to the housing. The first end of the gripper rod carries a forked gripping member that is adapted to cooperate with an arc needle to join the tissue edges. The arc needle is pivotally mounted to the housing for oscillation during a stitching operation. The second end of the gripper rod that is positioned within the housing is driven to oscillate along an arcuate path thereby causing a corresponding, symmetrical arcuate movement of the forked gripping member. The arcuate movement of the forked gripping member and the oscillating movement of the arc needle are performed in unison due to the drive arrangement of the suturing apparatus.

Additional objects and features of the suturing apparatus of the present invention will become more readily apparent from the following detailed description of a preferred embodiment thereof when taken in conjunction with the drawings wherein like reference numerals refer to corresponding parts in the several views.

DETAILED DESCRIPTION OF THE PREFERRED EMBODIMENTS

Figure 1:
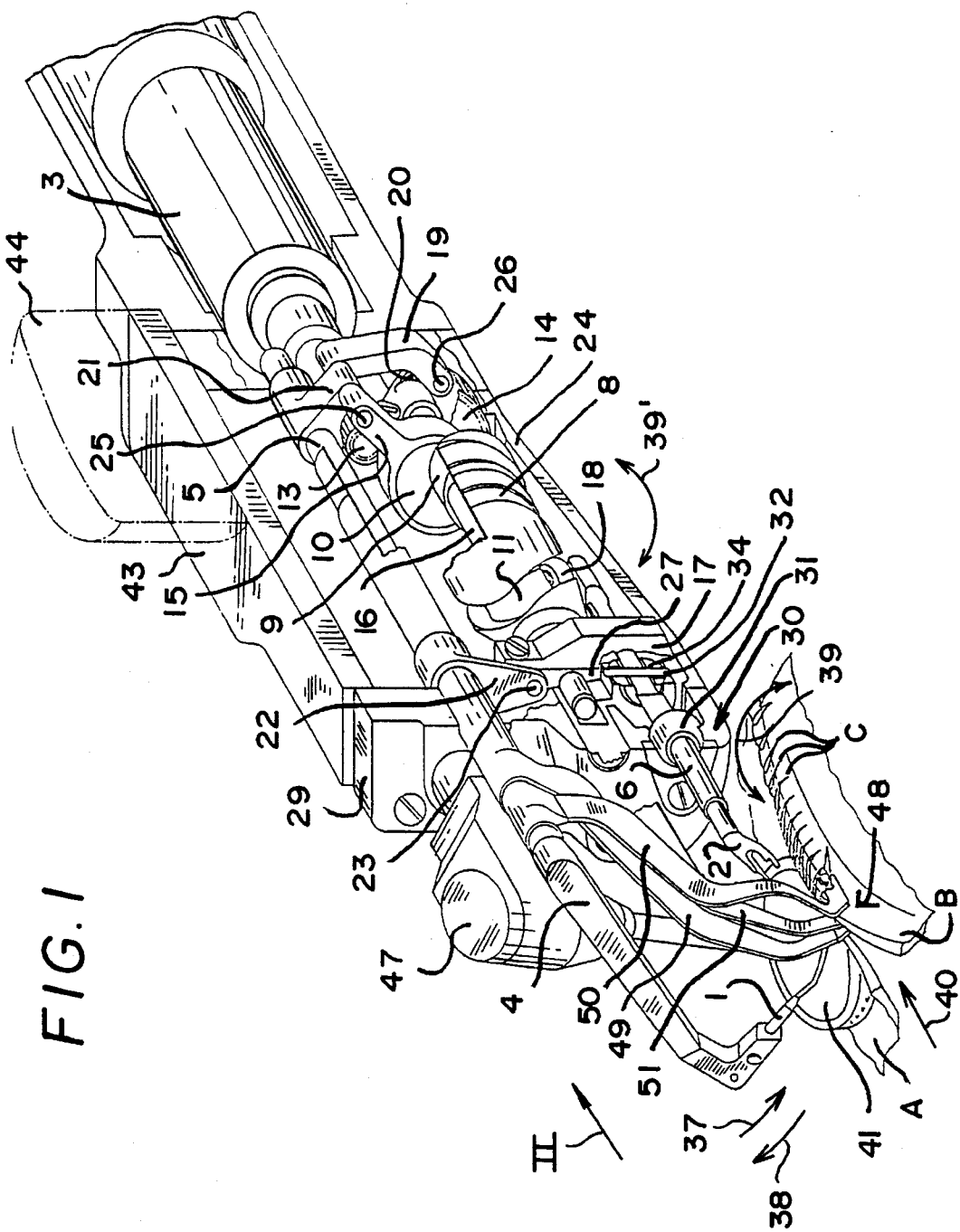
FIG. 1 is a perspective view of the suturing apparatus of the present invention with portions of the apparatus being removed for clarity.

The suturing apparatus of the invention, as best seen in FIG. 1, includes an arc needle 1 and a forked rocking gripper or loop catcher 2. An electric DC motor 3 is provided to drive the arc needle 1 and the rocking gripper 2 in unison as will be more fully described below. The arc needle 1 is provided at one end of a needle lever 4 that projects radially from a shaft 5 used to drive arc needle 1. On the other hand, rocking gripper 2 is mounted on a gripper rod 6.

By means of reduction gearing 7, DC motor 3 drives a control roller 8 that includes a needle drive cam 9, a gripper drive cam 10 and a gripper drive channel 11. The reduction gearing 7 actually consists of a pinion 13 carried by an output shaft 12 of the DC motor 3 and a gear 14 that is coaxial with and connected to control roller 8 and which meshes with pinion 13.

Although not particularly shown in the drawings, needle drive cam 9 cooperates through a linkage (not shown) with the needle shaft 5. This linkage acts on a drive arm (also not shown) that projects radially from the needle shaft 5. The gripper drive cam 10 cooperates by means of a linkage 15, a pivot shaft 16 and a swivel plate 17 with the gripper rod 6. The gripper drive channel 11 receives a spherical radial projection 18 carried by the end of gripper rod 6 remote from rocking gripper 2. Projection 18 is actually constituted by a spherical roller rotatably supported on a radial pin (not labeled) that is formed as part of gripper rod 6.

Linkage 15 is connected by a bracket 19 to a drive arm 20 that radially projects from pivot shaft 16. Linkage 15 is furthermore pivotally connected to a guide arm 21 that is rotatably supported by and radially projects from needle shaft 5. The swivel plate 17 is suspended from a support arm 22 that extends radially relative to needle shaft 5. Support arm 22 itself is freely rotatably mounted about needle shaft 5. Swivel plate 17 is attached to support arm 22 through a support bolt 23 that extends parallel to needle shaft 5 from support arm 22 and which is received in a bore (not labeled) formed in swivel plate 17. The swivel plate 17 is adjustable relative to the support bolt 23 such that the distance between that end of swivel plate 17 through which gripper rod 6 extends and both needle shaft 5 and pivot shaft 16 can be changed.

Needle shaft 5 and pivot shaft 16 run parallel to each other in the longitudinal direction of the suturing apparatus and are rotatably supported in housing 24. The control roller 8 and its associated gear 14 are rotatably supported on pivot shaft 16 between swivel plate 17 and connection bracket 19. The output shaft 12 of DC motor 3 runs parallel to needle shaft 5 and to pivot shaft 16. In addition, shaft 25, about which linkage 15, guide arm 21 and connection bracket 19 are mutually pivotable, and shaft 26, about which connection bracket 19 and radial drive arm 20 of pivot shaft 16 are mutually pivotable, are further parallel to needle shaft 5. The distance between pivot shaft 26 and the longitudinal axis of pivot shaft 16 can be changed and adjusted, causing a corresponding change in the angle by which pivot shaft 16 is pivoted to-and-fro.

Between support arm 22 and gripper rod 6, swivel plate 17 cooperates with a parallelepipedic slide block 27 positioned on pivot shaft 16. The slide block 27 is able to reciprocate in a central longitudinal slot 28 (see FIGS. 3 and 4) with slot 28 having a width "b" substantially equal to the width of slide block 27 but having a length "l" which is greater than the length of slide block 27.

Figure 3:
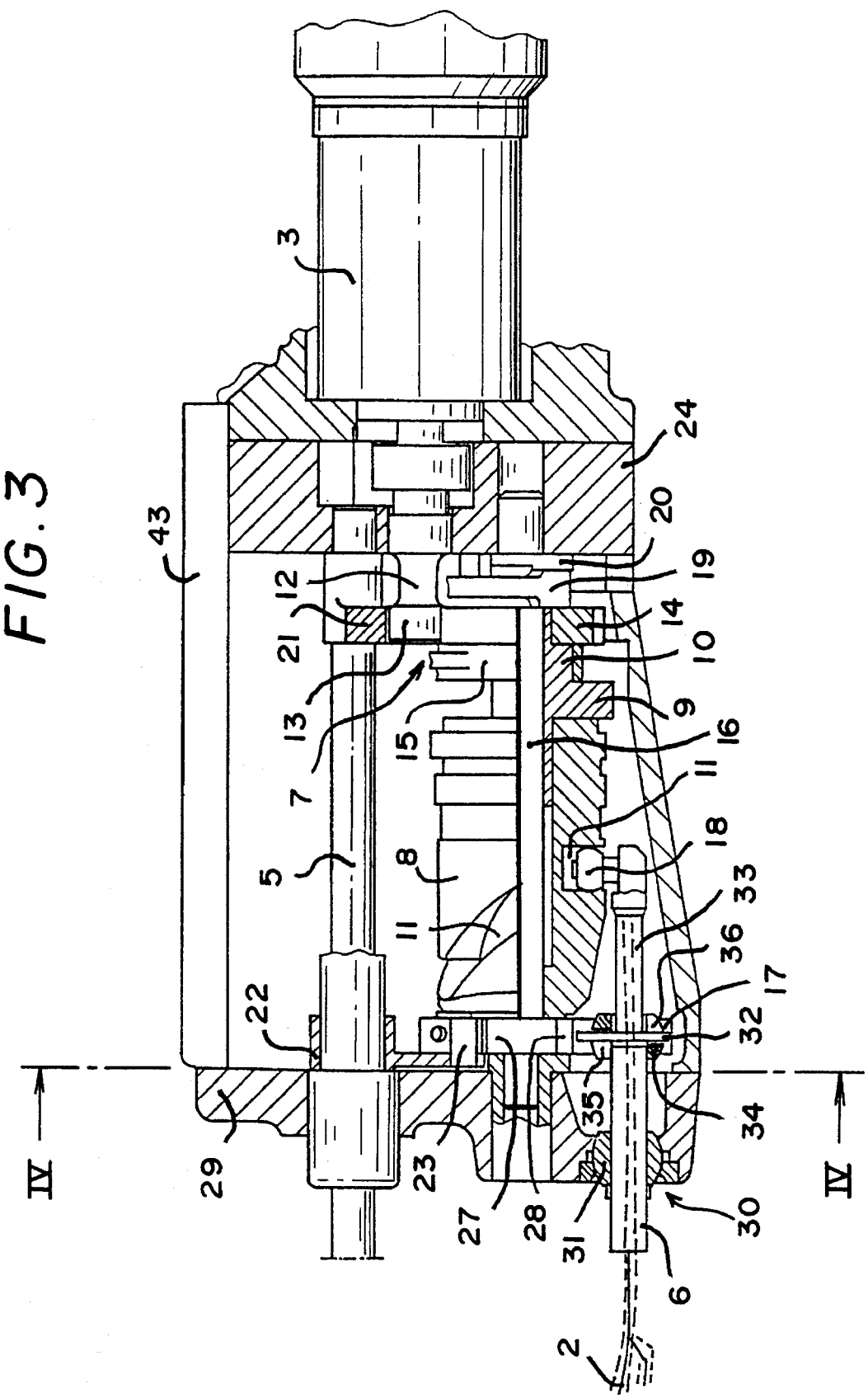
FIG. 3 is a longitudinal sectional view generally taken along line III—III of FIG. 2.
Figure 4:
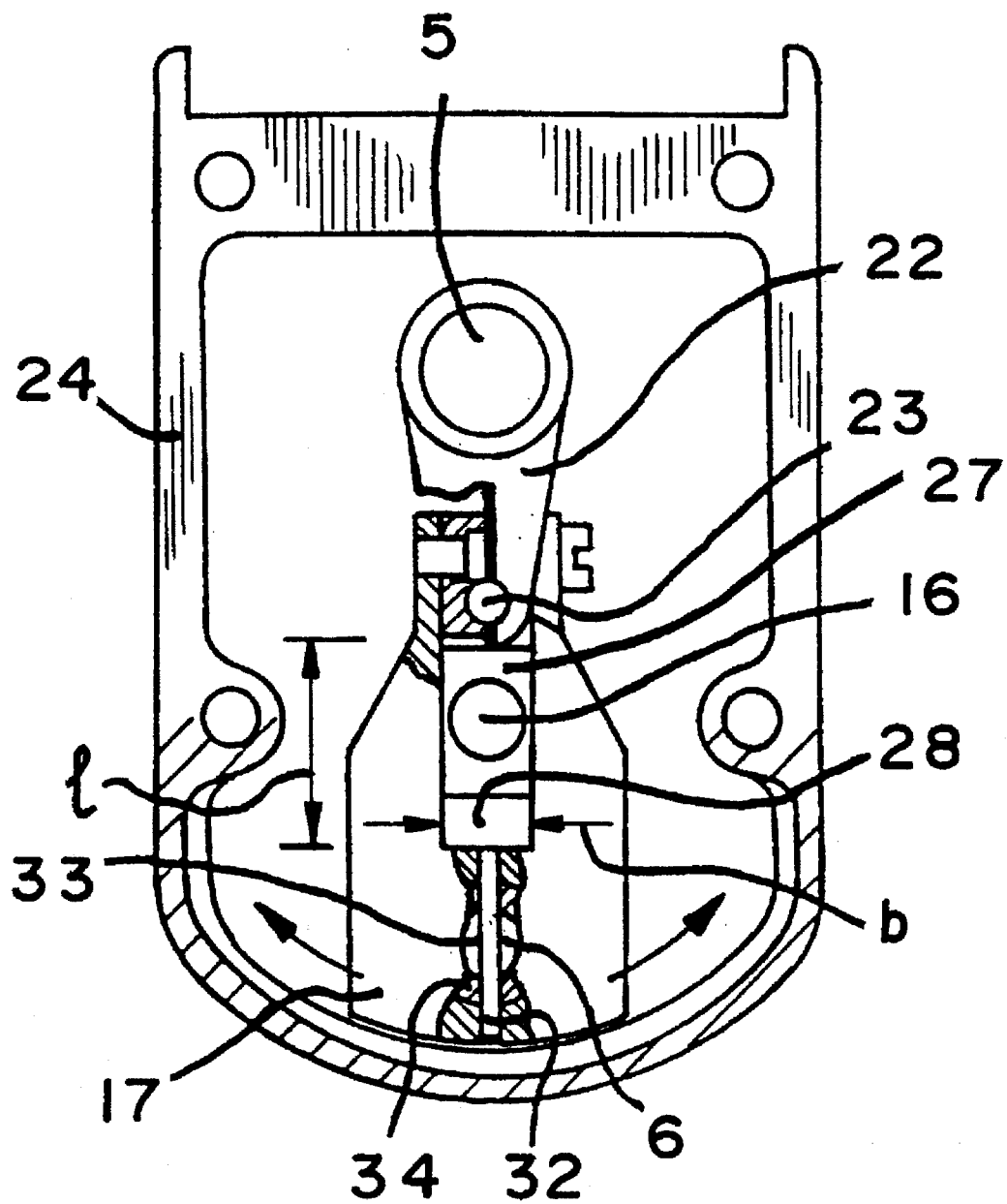
FIG. 4 is a cross-sectional view taken along line IV—IV of FIG. 3.

As best shown in FIG. 3, gripper rod 6 passes through front wall 29 of housing 24 at 30 while being pivotable, axially displaceable, and rotatable relative to front wall 29 of housing 24 by means of a ball 31. More specifically, gripper rod 6 is axially displaceable and rotatable in ball 31. The ball 31 itself is universally movable in front wall 29 of housing 24 like the ball of a universal joint.

Swivel plate 17 and slide block 27 of pivot shaft 16 are mounted between front wall 29 of housing 24 and the control roller 8. The support arm 22 of swivel plate 17 rests against the inside of front wall 29. Gripper rod 6 passes through swivel plate 17 between ball 31 and control roller 8.

Gripper rod 6 is non-rotatably affixed by a cross-pin 32 to swivel plate 17. Actually, cross-pin 32 extends in the longitudinal direction of swivel plate 17 and passes through a longitudinal slot 33 provided in gripper rod 6. A ball joint 34 is positioned between gripper rod 6 and swivel plate 17. With this arrangement, gripper rod 6 is supported in an axially displaceable manner within ball joint 34 which, in turn, is rotatable in swivel plate 17 about cross-pin 32 and is pivotable in the respective rotational position in swivel plate 17 about an axis perpendicular to cross-pin 32 and the longitudinal axis of gripper rod 6. For this purpose, cross-pin 32 passes through the center of ball joint 34 which comprises two diametrically opposed longitudinal slots 35, 36 that receive cross-pin 32. Slots 35 and 36 extend in the same plane, namely the plane containing the cross-pin 32 and the longitudinal axis of gripper rod 6, i.e., the plane in the drawing of FIG. 3 wherein rocking gripper 2 is shown in its central position.

The present suturing apparatus is particularly useful in suturing together edges of tissue, for example two tissue edges A and B. In accordance with the invention, arc needle 1 oscillates in the direction indicated by arrows 37 and 38, in order to transversely pierce the tissue edges A and B. The rocking gripper 2 cooperates with arc needle 1 to form stitches by pivoting to-and-fro in unison with the oscillation of arc needle 1. Rocking gripper 2 actually moves along an arcuate path 39 over the tissue edges A, B which are jointly made to advance stepwise in the direction of arrow 40 in FIG. 1 to produce a single-thread overcast stitching C.

Two circular advance discs 41,42 are provided for the stepwise advance of the tissue edges A, B in the direction of arrow 40 and are driven by an electric stepping motor 44 mounted on housing cover 43. Discs 41 and 42 are drivingly connected to motor 44 by means of a power dividing gearing arrangement (not shown) so as to rotate intermittently in opposing directions as indicated by arrows 45 and 46 whenever arc needle 1 is positioned outside of the tissue edges A, B. The power dividing gearing arrangement actually cooperates with two shafts (not shown) that extend parallel to needle shaft 5 and which are rotatably supported in housing 24. Each of these shafts cooperate through a bevel gear unit 47 with the right and left advance discs 41 and 42 respectively.

The suturing apparatus is further provided with forceps 48 for supporting the tissue edges A, B in the region of the path of motion of arc needle 1 transverse to edges A, B during suturing. The opening and closing of forceps 48 are synchronized with the motion of arc needle 1. Forceps 48 actually comprise a right leg 49 and a left leg 50. The two legs 49, 50 are mounted on opposite sides of a stationary middle arm 51 projecting forward from front wall 29 and are pivoted to a closed position prior to each piercing stroke of arc needle 1 into tissue edges A, B for the purpose of keeping the two tissue edges A, B together by pressing each tissue edge against a respective side of the middle arm 51. Following the ensuing exit of arc needle I from tissue edges A, B, legs 49 and 50 are pivoted to an open position so as to release the tissue edges A, B.

Figure 2:
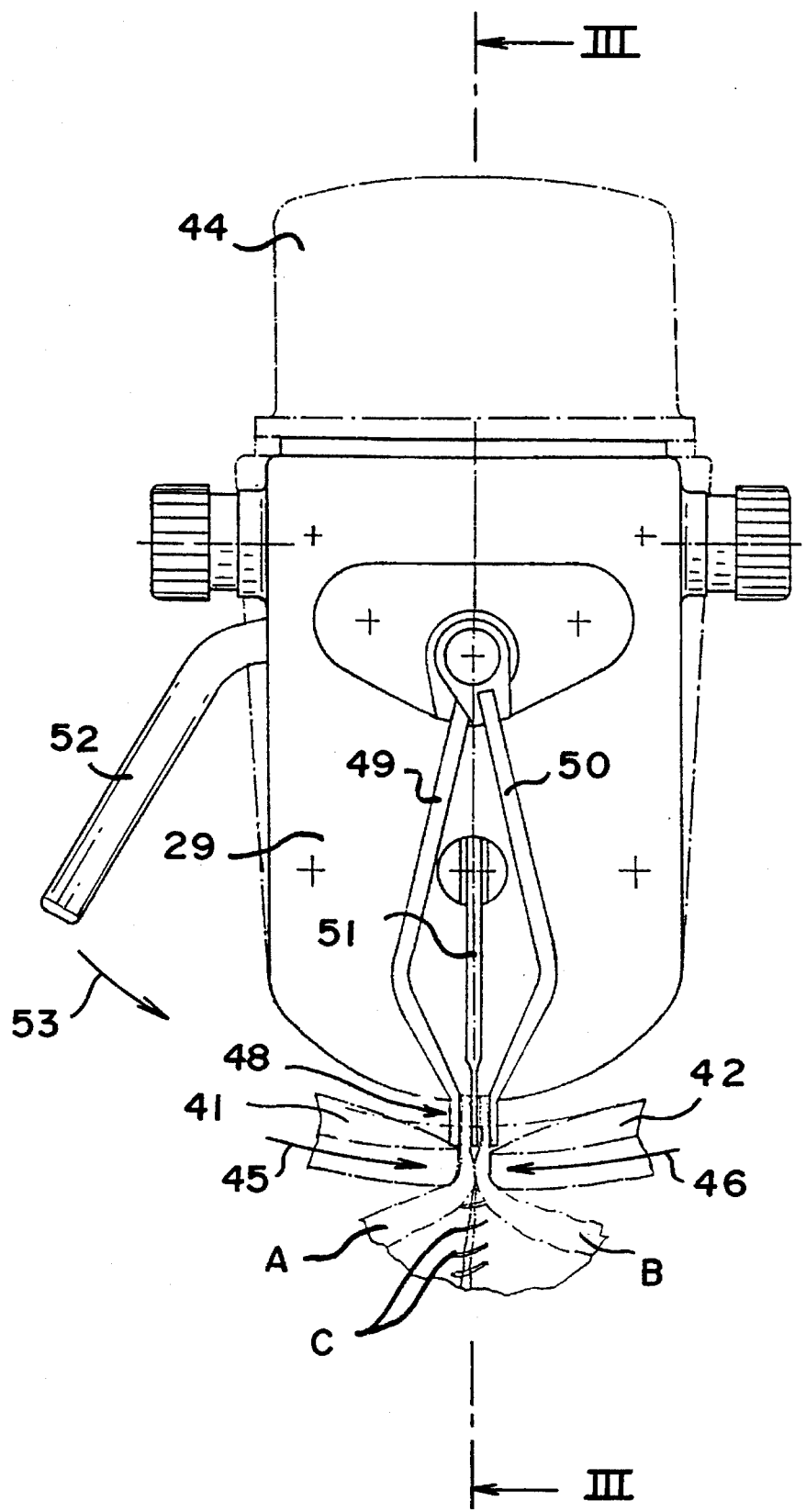
FIG. 2 is an enlarged front view of the suturing apparatus as viewed in the direction of arrow II of FIG. 1, shown without the arc needle and the rocking gripper for clarity.

In order to be able to insert the tissue edges A, B prior to suturing into the suturing apparatus and to remove them after suturing, the advance mechanism and the forceps 48 must be lifted. This is implemented using a hand lever 52 projecting from housing 24. When hand lever 52 is pivoted in the direction of arrow 53 in FIG. 2, the two advance discs 41,42 and legs 49, 50 spread apart.

The path of motion 39 of rocking gripper 2 is determined by the motion, induced by the swivel plate 17, of the gripper rod 6 inside housing 24 along an arcuate path 39'. The two paths of motion 39, 39' are symmetrical with the passage location 30 of gripper rod 6 to front wall 29, with, the center of symmetry being the center of ball 31. Illustratively, if gripper rod 6 moves from the right end of its path 39' shown in FIG. 1 toward the left end, then rocking gripper 2 will move from the left end of its path 39 to its right end as shown in FIG. 1. The suspension of the swivel plate 17 by means of the pivotable support arm 22 and the manner in which it is slidably guided along oscillating slide block 27 assure that the arc of the path of motion 39' of gripper rod 6 shall be relatively deep and narrow and that the arc of the path of motion 39 of rocking gripper 2 shall be correspondingly high and narrow.

Because gripper rod 6 is irrotatably fixed by cross-pin 32 to swivel plate 17 and because gripper rod 6 cooperates with control roller 8 by means of the radial projection 18 entering the gripper drive channel 11, the rotating and shifting of rocking gripper 2 about and along the longitudinal axis of gripper rod 6 required to pick-up, the thread loops, to position and to strip-off, will be effectively carried out.

By the above description, it should be readily apparent that the suturing apparatus of the present invention is provided with a rocking gripper arrangement that enables forked rocking gripper 2 to effectively cooperate with arc needle 1 to perform suturing stitches on tissues A, B. Although described with respect to a preferred embodiment of the invention, it should be readily understood that various changes and/or modifications can be made to the invention without departing from the spirit thereof. In general, the invention is only intended to be limited by the scope of the following claims.

I claim:

1. A suturing apparatus for use in joining tissue edges using single-thread overcast stitches comprising:

a housing having a front wall;

an arc needle pivotally mounted to said housing for oscillation during a stitching operation;

a gripper rod having a first end portion projecting through the front wall of said housing and a second end portion positioned within said housing;

means for supporting said gripper rod, at a support location between the first and second end portions thereof, for pivotal, rotatable and axial shiftable movement relative to said housing;

a forked gripping member carried by the first end portion of said gripper rod; and means acting on the second end portion of said gripper rod for causing said second end portion to oscillate along an arcuate path within said housing and causing a corresponding, symmetrical arcuate movement of said forked gripping member with said support location defining a center of symmetry for the arcuate movements such that, during a stitching operation, when said arc needle is oscillated to perform a stitching operation on a pair of aligned tissue edges, said forked gripping member will oscillate over the tissue edges in unison with said arc needle.

2. A suturing apparatus as claimed in claim 1, wherein said gripper rod is rotatably and axially displaceably supported in a universal joint mounted in the front wall of said housing.

3. A suturing apparatus as claimed in claim 1, further comprising a support arm pivotally supported about a first pivot shaft in said housing and a slide block positioned between said support arm and said gripper rod, said means acting on the second end portion of said gripper rod including a swivel plate pivotally connected to said support arm through a second pivot shaft, said swivel plate being further connected to said gripper rod such that movement of said swivel plate causes said gripper rod to move along said arcuate path, said slide block being pivotable to-and-fro about a third pivot shaft that is parallel to both said first and second pivot shafts.

4. A suturing apparatus as claimed in claim 3, wherein said swivel plate is adjustable relative to said second pivot shaft.

5. A suturing apparatus as claimed in claim 3, further comprising a gripper drive cam rotatably mounted within said housing about a fourth pivot shaft, a guide arm pivotally mounted within said housing about a fifth pivot shaft, and a linkage pivotally connected to said guide arm through a sixth pivot shaft and engaging said gripper drive cam, said slide block being interconnected through said linkage to said gripper drive cam such that rotation of said gripper drive cam causes said slide block to pivot to-and-fro, said fourth, fifth and sixth pivot shafts being arranged parallel to one another within said housing.

6. A suturing apparatus as claimed in claim 5, further comprising a connection bracket pivotally interconnecting said guide arm and said linkage to a radial drive arm, said radial drive arm being carried by said third pivot shaft for rotation with said slide block, said connection bracket being pivotally attached to said linkage and said guide arm through said sixth pivot shaft and said connection bracket being pivotally attached to said radial drive arm by a seventh pivot shaft, said third, sixth and seventh pivot shafts being parallel.

7. A suturing apparatus as claimed in claim 6, wherein the distance between said third and seventh pivot shafts is adjustable.

8. A suturing apparatus as claimed in claim 3, further comprising a cross-pin for non-rotatably connecting said gripper rod to said swivel plate and a ball joint, positioned in said swivel plate, to which said gripper rod is attached for pivotal and axial movement, said ball joint substantially surrounding said gripper rod and including two diametrically opposed and longitudinally extending slots, said gripper rod being further provided with a longitudinal slot, said cross-pin extending within the longitudinal slots in said ball joint and said gripper rod, whereby said ball joint can be rotated about said cross-pin and is pivotable about an axis perpendicular to a plane defined by the longitudinal slots provided in said ball joint.

9. A suturing apparatus as claimed in claim 3, further comprising a control roller provided with a gripper drive channel that is engaged by a radial projection formed at the second end portion of said gripper rod, said gripper drive channel defining a cam such that rotation of said control roller causes said gripper rod to the axially displaced.

10. A suturing apparatus as claimed in claim 1, further comprising a control roller provided with a gripper drive channel that is engaged by a radial projection formed at the second end portion of said gripper rod, said gripper drive channel defining a cam such that rotation of said control roller causes said gripper rod to be axially displaced.

11. A suturing apparatus as claimed in claim 9, wherein said swivel plate is positioned between the front wall of said housing and said control roller and wherein the radial projection of said gripper rod is spherical.

12. A suturing apparatus as claimed in claim 10, wherein the radial projection of said gripper rod is formed by a roller rotatably supported on a radial pin of the gripper rod.

13. A suturing apparatus as claimed in claim 6, further comprising a control roller provided with a gripper drive channel that is engaged by a radial projection formed at the second end portion of said gripper rod, said gripper drive channel defining a cam such that rotation of said control roller causes said gripper rod to be axially displaced.

14. A suturing apparatus as claimed in claim 13, wherein said swivel plate is positioned between the front wall of said housing and said control roller and wherein the radial projection of said gripper rod is spherical.

15. A suturing apparatus as claimed in claim 14, wherein said control roller is integrally formed with said cam and is mounted upon said fourth pivot shaft.

16. A suturing apparatus as claimed in claim 15, further comprising an electric DC motor drivingly connected to said control roller.

17. A suturing apparatus as claimed in claim 16, further including a reduction gearing assembly between said DC motor and said control roller.

\* \* \* \* \*